United States Patent [19]

Anderson

[11] 4,276,230

[45] Jun. 30, 1981

[54] CYANO-3-PHENOXYBENZYL N-1-(1-NAPHTHYL) ETHYLCARBAMATE

[75] Inventor: Richard J. Anderson, Palo Alto, Calif.

[73] Assignee: Zoecon Corporation, Palo Alto, Calif.

[21] Appl. No.: 142,518

[22] Filed: Apr. 21, 1980

[51] Int. Cl.³ .................. C07C 121/75; C07C 121/78
[52] U.S. Cl. ........................ 260/465 D; 260/453 AR; 260/465 F; 424/304
[58] Field of Search ........................ 260/465 D, 465 F

[56] References Cited

U.S. PATENT DOCUMENTS 4,206,124  6/1980  Martel et al. ................ 260/465 F X

OTHER PUBLICATIONS

Ruzo et al., Tetrahedron Letters No. 35, pp. 3045–3048 (1976).

Primary Examiner—Dolph H. Terrence
Attorney, Agent, or Firm—Donald W. Erickson; Thomas T. Gordon

[57] ABSTRACT

Diastereomeric esters of 2-phenylamino-3-methyl-butanoic acids, novel intermediates therefor, synthesis thereof, and the use of said esters for the control of pests.

4 Claims, No Drawings

CYANO-3-PHENOXYBENZYL N-1-(1-NAPHTHYL) ETHYLCARBAMATE

This invention relates to diastereomeric esters of amino acids, novel intermediates therefor, synthesis thereof, and the use of said esters for the control of pests.

The esters of amino acids of the following formula (A):

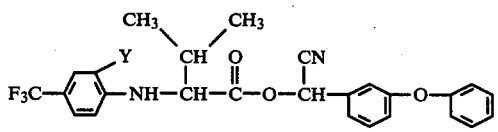

wherein,

Y is hydrogen or chloro; and the acid is the R configuration and the alcohol is the S configuration or a mixture of the S configuration and the R configuration are useful for the control of pests.

Certain esters of substituted-phenylamino acids have been described by Henrick & Garcia, Offenlegungsschrift No. 28 12 169, as being effective agents for the control of pests such as insects and acarids, acting in the manner of synthetic pyrethroids. The diastereomer and diastereomeric pairs of formula (A) herein possess greatly improved pesticidal activity as compared to the RS,SR,-RR, SS, diastereomeric mixture.

The compounds of formula (A) can be prepared by the reaction of an acid of formula (I), in its R configuration, with the S enantiomer or the R,S racemic mixture of α-cyano-3-phenoxybenzyl alcohol (II).

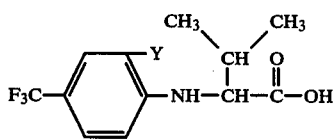

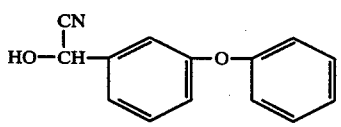

The above esterification can be carried out at a low temperature in the presence of 4-dimethylaminopyridine and dicyclohexylcarbodiimide.

The acid (I) is prepared from (R)-valine by conversion first to (R)-2-bromo-3-methylbutanoic acid and reaction of the latter with 4-trifluoromethylaniline to give the 4-substituted phenylamino acid. This can be chlorinated by use of N-chlorosuccinimide to prepare an acid of formula (I) wherein Y is chloro.

In accordance with the present invention, the R and the S enantiomers of the alcohol II are made by reacting racemic α-cyano-3-phenoxybenzyl alcohol with (R)-1-(1-naphthyl)ethyl isocyanate in the presence of 4-dimethylaminopyridine and a solvent such as toluene or benzene. The resulting carbamate is separated into its two diastereomers by liquid chromatography. The R,R isomer is further purified by crystallization and the R,S isomer, by repeated chromatography. Alternatively, the diastereomers can be separated from the mixture without initial chromatographic separation by adding a seed crystal of substantially optically pure R,R carbamate and crystallizing out the R,R isomer. Each of the two separated diastereomers, in a solvent such as benzene, is reacted with trichlorosilane and triethylamine, at elevated temperature, to give the resulting R and S enantiomer of formula II.

Alternatively, in accordance with the present invention, the R and S enantiomers of the alcohol II can be made by reacting racemic α-cyano-3-phenoxybenzyl alcohol with (S)-1-(1-naphthyl)ethyl isocyanate in place of (R)-1-(1-naphthyl)ethyl isocyanate using the procedures described above.

In the prior art, synthetic pyrethroid esters containing the α-cyano-3-phenoxybenzyl alcohol moiety have been separated into their diastereomers after esterification, rather than by taking the desired acid enantiomer and the desired alcohol enantiomer and then esterifying them to make the diastereomer of the ester compound. Cf. Warnant et al., U.S. Pat. Nos. 4,133,826 & 4,151,195, and Stoutamire, U.S. Pat. No. 4,176,195. α-Cyano-3-phenoxybenzyl alcohol is a labile molecule and stereoselective preparation or the resolution of the racemic alcohol has not previously been successful. CF. Elliott et al, Pestic Sci 1978,9,105–111.

The compounds of formula (A) are effective on many different insects and on acarids. The compounds are effective control agents for insects such as mosquitoes, flies, aphids, weevils and acarids such as the spider mite and ticks.

Herein, and in the appended claims, unless otherwise provided, the first letter refers to the configuration of the acid moiety and the second letter refers to the configuration of the alcohol moiety. For example, "RS" diastereomer means $R_{acid}$-$S_{alcohol}$.

The following examples are provided to illustrate the practice of the present invention. Temperature is given in degrees Centigrade. RT means room temperature.

EXAMPLE 1

To 12.4 g (72.5 mmol) of purified (R)-1-(1-naphthyl)ethylamine in 130 ml of dry toluene is added, with stirring, gaseous hydrogen chloride for about 30 minutes, during which time an additional 100 ml of toluene is added to facilitate stirring. Phosgene is bubbled into the separation, at RT, for about 20 minutes and then at reflux for 2 hours. Phosgene addition is stopped and the solution is heated at reflux for another 1.5 hours. The toluene is distilled off at atmospheric pressure and the residue is distilled (short path) at 0.30 mm to yield (R)-1-(1-naphthyl)ethyl isocyanate.

A solution of 11.0 g (56.0 mmol) of (R)-1-(1-naphthyl)ethyl isocyanate, 12.6 g (56.0 mmol) of racemic α-cyano-3-phenoxybenzyl alcohol and 150 mg of 4-dimethylaminopyridine in 75 ml of toluene is heated at 50°, under nitrogen, for about 20 hours. The reaction mixture is cooled and poured into ether and 5% HCl. The organic phase is separated and washed with saturated sodium bicarbonate and with brine and is dried over sodium sulfate. Removal of solvent gives (R,S)-α-cyano-3-phenoxybenzyl (R)-N-1-(1-naphthyl)ethylcarbamate.

EXAMPLE 2

The (R,S)-α-cyano-3-phenoxybenzyl (R)-N-1-(1-naphthyl)ethylcarbamate is purified by liquid chromatography on silica columns using 23% ether/hexane. The first fraction, containing a high ratio of the faster eluting diastereomer, is collected and combined with several ml of ether. Hexane is added until crystals begin to form. This is allowed to crystallize overnight. The resulting crystals are collected and washed with hexane, giving (R)-α-cyano-3-phenoxybenzyl (R)-N-1-(1-naphthyl)ethylcarbamate, m.p. 121.5°–122°, specific rotation $[\alpha]_D^{25} = -15.2°$ (c=10 mg/ml in CHCl$_3$), diastereomer purity = ~99%.

EXAMPLE 3

The second fraction obtained from purification of (R,S)-α-cyano-3-phenoxybenzyl (R)-N-1-(1-naphthyl)ethylcarbamate by liquid chromatography, from Example 2 above, which second fraction contains a high ratio of the slower eluting diastereomer, is collected. Since the slower eluting diastereomer does not readily crystallize out of solution, the fraction is further purified by liquid chromatography, using ether/hexane, and collection again of the second fraction. This purification process is continued until a substantially diastereomerically pure sample of the compound (S)-α-cyano-3-phenoxybenzyl (R)-N-1-(1-naphthyl)ethylcarbamate is obtained, m.p. 41°–41.5°, specific rotation $[\alpha]_D^{25} = -19.6°$ (c=10 mg/ml in CHCl$_3$), diastereomer purity = ~98%.

EXAMPLE 4

To 1.99 g (4.7 mmol) of (R)-α-cyano-3-phenoxybenzyl (R)-N-1-(1-naphthyl)ethylcarbamate in 20 ml of benzene is added 725 μl (525 mg, 5.2 mmol) of triethylamine. The solution, under nitrogen, is stirred while 505 μl (675 mg, 5.0 mmol) of trichlorosilane is added. The reaction is warmed to 50° for 2.5 hours, and is then poured into saturated ammonium chloride and ether. The organic fraction is washed again with saturated ammonium chloride and then with brine (3×), and is dried over sodium sulfate overnight in the freezer. Solvent is removed by rotoevaporation, and the residue is washed repeatedly with hexane to remove the isocyanate. The urea contamination is removed by dissolving the product in ether/hexane (~1:1), and the solvent is then removed. Purification by thin layer chromatography (tlc) on silica gel plates developed in 30% ethylacetate/hexane yields the product, which is then dissolved in trichloromethane. The solvent is removed, giving (R)-α-cyano-3-phenoxybenzyl alcohol, specific rotation $[\alpha]_D = +15.2°$ (c=10 mg/ml in acetone).

EXAMPLE 5

To a solution of 2.91 g (6.99 mmol) of (S)-α-cyano-3-phenoxybenzyl (R)-N-1-(1-naphthyl)ethylcarbamate in 30 ml of dry benzene under a nitrogen atmosphere is added 1.07 ml (0.78 g, 7.7 mmol) of triethylamine followed immediately by 0.75 ml (1.0 g, 7.4 mmol) of trichlorosilane. The reaction is heated at 50° for 3 hours and is then worked up and purified following the procedure of Example 4. The more polar band on the tlc plate is removed and extracted with trichloromethane to yield (S)-α-cyano-3-phenoxybenzyl alcohol, specific rotation $[\alpha]_D^{25} = -14.6°$ (c=11 mg/ml in acetone).

EXAMPLE 6

Approximately 0.5 g of the compound (R,S)-α-cyano-3-phenoxybenzyl (R)-N-1-(1-naphthyl)ethylcarbamate from Example 1 is dissolved in ~1 ml of ether and a few drops of hexane are added. To this is added a seed crystals of ~99% optically pure (R)-α-cyano-3-phenoxybenzyl (R)-N-1-(1-naphthyl)ethylcarbamate from Example 2, and the mixture is allowed to crystallize overnight. The solid is separated out and washed with hexane several times. The solid shows a diastereomer purity of 72% (R)-α-cyano-3-phenoxybenzyl (R)-N-1-(1-naphthyl)carbamate. Several additional crystallizations of this solid gives carbamate of 98% diastereomeric purity.

The separated mother liquor is purified by liquid chromatography as in Example 3 to give (S)-α-cyano-3-phenoxybenzyl (R)-N-1-(1-naphthyl)ethylcarbamate.

EXAMPLE 7

(S)-α-Cyano-3-phenoxybenzyl (R)-2-(2-chloro-4-trifluoromethylphenylamino)-3-methylbutanoate, prepared as described in application Ser. No. 142,522, filed on Apr. 21, 1980, is tested on III instar *Heliothis virescens* larvae giving an LD$_{50}$ of 0.0181. The test method is as follows.

Two groups of 10 each of 0–24 hr III instar *Heliothis virescens* larvae were treated with 1 μl of the test compound in acetone at different dosage rates by application to the dorsum of the thorax. Two groups of 10 each are treated identically with 1 μl acetone as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control group using Abbott's formula. The toxicity is expressed as LD$_{50}$, which is the dosage, in μg per insect, required to kill 50% of the test insects.

EXAMPLE 8

Following the procedure of Example 1, (S)-1-(1-naphthyl)ethylamine is used in place of (R)-1-(1-naphthyl) ethylamine to yield (R,S)-α-cyano-3-phenoxybenzyl (S)-N-1-(1-naphthyl)ethylcarbamate which is separated, using the procedures of Examples 2 and 3, into (S)-α-cyano-3-phenoxybenzyl (S)-N-1-(1-naphthyl)ethylcarbamate and (R)-α-cyano-3-phenoxybenzyl (S)-N-1-(1-naphthyl)ethylcarbamate. The enantiomer, (S)-α-cyano-3-phenoxybenzyl alcohol, is then obtained using the process of Example 5.

What is claimed is:

1. The compound, α-cyano-3-phenoxybenzyl N-1-(1-naphthyl)ethylcarbamate.

2. The diastereomer, (S)-α-cyano-3-phenoxybenzyl (R)-N-1-(1-naphthyl)ethylcarbamate, according to claim 1.

3. The diastereomeric pair, (R,S)-α-cyano-3-phenoxybenzyl (R)-N-1-(1-naphthyl)ethylcarbamate, according to claim 1.

4. The diastereomer, (S)-α-cyano-3-phenoxybenzyl (S)-N-1-(1-naphthyl)ethylcarbamate, according to claim 1.

* * * * *